United States Patent [19]

Mohan

[11] 4,053,430

[45] Oct. 11, 1977

[54] AQUEOUS CHEMILUMINESCENT SYSTEMS

[75] Inventor: Arthur Gaudens Mohan, Somerville, N.J.

[73] Assignee: American Cyanamid Company, Stamford, Conn.

[21] Appl. No.: 705,863

[22] Filed: July 16, 1976

[51] Int. Cl.$^2$ ............................................. C09K 11/06
[52] U.S. Cl. ...................... 252/188.3 CL; 260/293.73; 560/142; 560/146
[58] Field of Search ...................... 260/479 S, 293.73; 252/188.3 CL

[56] References Cited

U.S. PATENT DOCUMENTS

| | | | |
|---|---|---|---|
| 3,453,099 | 7/1969 | Popoff | 260/470 |
| 3,597,362 | 8/1971 | Bollyky | 252/188.3 CL |
| 3,704,231 | 11/1972 | Bollyky | 252/188.3 CL |
| 3,749,679 | 7/1973 | Rauhut | 252/188.3 CL |
| 3,781,329 | 12/1973 | Bollyky | 260/479 S |
| 3,816,326 | 6/1974 | Bollyky | 252/188.3 CL |
| 3,970,660 | 7/1976 | Bollyky | 252/188.3 CL |

*Primary Examiner*—Benjamin R. Padgett
*Assistant Examiner*—Deborah L. Kyle
*Attorney, Agent, or Firm*—Gordon L. Hart

[57] ABSTRACT

This invention relates to novel water-soluble esters of oxalic acid, and to compositions that are useful for generating chemiluminescent emission by reacting said esters of oxalic acid with hydrogen peroxide in the presence of water and a fluorescent compound, and to a process for generating chemiluminescent emission by using said compositions.

30 Claims, No Drawings

AQUEOUS CHEMILUMINESCENT SYSTEMS

The invention described herein was made in the performance of work under NASA Contract Number NAS5-22303 and is subject to the Provisions of Section 305 of the National Aeronautics and Space Art of 1958 (72 Stat. 435; 42 USC 2457).

BACKGROUND OF THE INVENTION

This invention relates to novel compounds and compositions containing them which are useful for the generation of chemiluminescent emission, that is, the generation of electromagnetic radiation at wavelengths between 330 and 1,000 nanometers by means of a chemical reaction.

The art of generating light via chemical energy, i.e. chemiluminescence, by the reaction of an oxalic acid ester with a hydroperoxide in the presence of a fluorescer compound in organic solvents has been disclosed in U.S. Pat. Nos. 3,816,326; 3,781,329; 3,749,679; 3,704,309 and 3,597,362. However, these esters and fluorescers have very poor efficiency in completely aqueous systems.

There is a need, therefore, for aqueous chemiluminescent compositions useful as emergency sources of light for automotive and marine safety purposes, as well as for a wide variety of other uses.

SUMMARY OF THE INVENTION

We have discovered the class of water-soluble esters of oxalic acid having the formula:

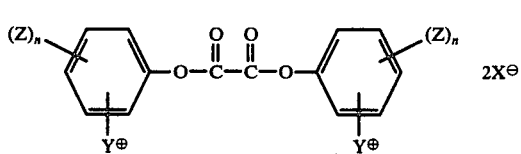

(I)

wherein Z represents chloro, fluoro, and bromo, $n$ is an integer from 1 to 2, $X^-$ is an anion and $Y^+$ represents a radical having an ammonium group and having the formula (II):

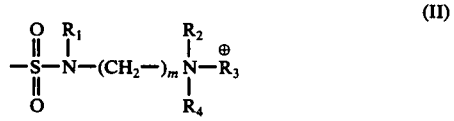

(II)

wherein $R_1$ represents alkyl having 1 to 6 carbon atoms, $R_2$ and $R_3$ independently represent $C_1$-$C_6$ alkyl or together with the nitrogen atom form a piperidine ring, $R_4$ is selected from hydrogen and alkyl having 1 to 6 carbon atoms, and $m$ is an integer from 1 to 4. When a diester of this formula is admixed with an aqueous mixture of a water soluble organic fluorescer compound, having spectral emission in the range from about 300 to 1,000 nanometers, and with hydrogen peroxide or a source of hydrogen peroxide, the mixture produces chemiluminescent emission of high intensity which lasts a usefully long period of time.

Typical esters of formula (I) which may be employed are those compounds wherein the anion is selected from chloride, bromide, fluoride, methanesulfonate, methosulfonate, trifluoromethanesulfonate, p-toluenesulfonate, and the like.

The oxalate esters in the chemiluminescent systems described in prior arts usually were dissolved for the use in organic solvents which would constitute most of the weight and volume of the system. Use of water instead of the organic solvents in the chemiluminescent system offers the following advantages:

1. Only the oxalate ester, the fluorescer and the hydroperoxide need to be packaged since water can readily be added at the point of use. This greatly increases the efficiency of the system on the basis of light output per unit of weight or volume of the packaged unit.
2. The potential for flammability of the organic solvent is reduced.
3. The cost of the system is reduced by substitution of water for the organic solvents.
4. The chemiluminescent reaction can be activated by addition of water to an inactive dry mixture of the required ingredients, utilizing dry sodium perborate or other solid hydroperoxide source.

DESCRIPTION OF THE PREFERRED EMBODIMENTS

In Formula I we prefer the compounds having an anion which is not oxidized by hydrogen peroxide in the chemiluminescent compositions.

The term "hydrogen peroxide compound", as used herein, means hydrogen peroxide or a compound that produces hydrogen peroxide by reaction or decomposition.

The novel oxalate esters of this invention may be obtained as the dihydrochloride by reacting two moles of a suitably substituted benzenesulfonamide with one mole of oxalyl chloride in an anhydrous organic solvent such as chloroform. The dihydrochloride may optionally be converted to the corresponding trifluoromethanesulfonate, methanesulfonate, p-toluenesulfonate, methosulfate, bromide or fluoride by suitable anionexchange methods which are well-known in the art. The dihydrochlorides may also be converted to quaternary ammonium salts by quaternization reactions which are well known.

Illustrative examples of compounds of formula (I) within the purview of this invention include the dihydrochlorides, dihydrobromides, dihydrofluorides, di(trifluoromethane) sulfonates, dimethanesulfonates, di-p-toluenesulfonates, dimethosulfonates and diquaternary ammonium salts of the following compounds:

bis{2,6-dichloro-4-[(2-dimethylaminoethyl)methylsulfamoyl]phenyl}oxalate
bis{2,4-dichloro-6-[(2-dimethylaminoethyl)methylsulfamoyl]phenyl}oxalate
bis{3-chloro-4-[(2-dimethylaminoethyl)methylsulfamoyl]phenyl}oxalate
bis{3-chloro-6-[(2-dimethylaminoethyl)methylsulfamoyl]phenyl}oxalate
bis{4-chloro-6-[(2-dimethylaminoethyl)methylsulfamoyl]phenyl}oxalate
bis{2,4-dibromo-4-[(2-dimethylaminoethyl)methylsulfamoyl]phenyl}oxalate
bis{2,6-dibromo-4-[(2-dimethylaminoethyl)methylsulfamoyl]phenyl}oxalate
bis{3-bromo-4-[(2-dimethylaminoethyl)methylsulfamoyl]phenyl}oxalate
bis{2,3-dibromo-4-[(2-dimethylaminoethyl)methylsulfamoyl]phenyl}oxalate bis{3-fluoro-4-[(2-dimethylaminoethyl)methylsulfamoyl]phenyl}oxalate
bis{2,5-dibromo-4-[(2-dimethylaminoethyl)methylsulfamoyl]phenyl}oxalate
bis{2-fluoro-4-[(2-dimethylaminoethyl)methylsulfamoyl]phenyl}oxalate
bis{2,4-dichloro-6-[(2-dimethylaminoethyl)n-hexylsulfamoyl]phenyl}oxalate
bis{2,6-dichloro-4-[(2-di-n-hexylaminoethyl)methylsulfamoyl]phenyl}oxalate
bis{2,3-dibromo-6-[(2-dimethylaminoethyl)i-propylsulfamoyl]phenyl}oxalate
bis{2,4-dibromo-6-[(4-dimethylaminobutyl)methylsulfamoyl]phenyl}oxalate
bis{2,6-dichloro-4-[(dimethylaminomethyl)methylsulfamoyl]phenyl}oxalate
bis{2,6-dibromo-4-[(2-di-n-propylaminoethyl)methylsulfamoyl]phenyl}oxalate
bis{2,4-dichloro-6-[(2-N-piperidylethyl)methylsulfamoyl]phenyl}oxalate
bis{2,4-dibromo-6-[(2-dimethylaminoethyl)n-hexylsulfamoyl]phenyl}oxalate
bis{2,6-dibromo-4-[(4-dimethylaminobutyl)methylsulfamoyl]phenyl}oxalate
bis{2,6-dibromo-4-[(2-di-n-hexylaminoethyl)methylsulfamoyl]phenyl}oxalate
bis{2,4-dichloro-6-[(2-piperidinoethyl)methylsulfamoyl]phenyl}oxalate, and the like Illustrative examples of substituted benzenesulfonamides which may be reacted with oxalyl chloride to prepare the compounds of this invention include:

3,5-dichloro-4-hydroxy-N-(2-dimethylaminoethyl)-N-methylbenzenesulfonamide
3,5-dichloro-2-hydroxy-N-(2-dimethylaminoethyl)-N-methylbenzenesulfonamide
3,4-dichloro-2-hydroxy-N-(2-dimethylaminoethyl)-N-methylbenzenesulfonamide
2,3-dichloro-4-hydroxy-N-(2-dimethylaminoethyl)-N-methylbenzenesulfonamide
2,5-dichloro-4-hydroxy-N-(2-dimethylaminoethyl)-N-methylbenzenesulfonamide
3,5-dibromo-4-hydroxy-N-(2-dimethylaminoethyl)-N-methylbenzenesulfonamide
3,5-dibromo-2-hydroxy-N-(2-dimethylaminoethyl)-N-methylbenzenesulfonamide
2-fluoro-4-hydroxy-N-(2-dimethylaminoethyl)-N-methylbenzenesulfonamide
3-fluoro-4-hydroxy-N-(2-dimethylaminoethyl)-N-methylbenzenesulfonamide
3-chloro-4-hydroxy-N-(2-dimethylaminoethyl)-N-methylbenzenesulfonamide
2-bromo-4-hydroxy-N-(2-dimethylaminoethyl)-N-methylbenzenesulfonamide
4-chloro-2-hydroxy-N-(2-dimethylaminoethyl)-N-methylbenzenesulfonamide
5-chloro-2-hydroxy-N-(2-dimethylaminoethyl)-N-methylbenzenesulfonamide
3,5-dichloro-2-hydroxy-N-(2-dimethylaminoethyl)-N-n-hexylbenzenesulfonamide
3,5-dichloro-4-hydroxy-N-(dimethylaminoethyl-N-methylbenzenesulfonamide
3,5-dichloro-4-hydroxy-N-(2-di-n-hexylaminoethyl)-N-methylbenzenesulfonamide
3,5-dibromo-4-hydroxy-N-(4-dimethylaminobutyl)-N-methylbenzenesulfonamide
3,5-dibromo-2-hydroxy-N-(2-dimethylaminoethyl)-N-n-hexylbenzenesulfonamide
3,5-dibromo-4-hydroxy-N-(2-di-n-propylaminoethyl)-N-methylbenzenesulfonamide
3,5-dichloro-2-hydroxy-N-(2-piperidinoethyl)-N-methylbenzenesulfonamide, and the like.

The benzenesulfonamides mentioned above may be prepared by reacting the corresponding substituted benzenesulfonyl chloride or benzenesulfonylfluoride with a suitable N-alkyl-N-(dialkylaminoalkyl)amine such as N,N,N'-trimethylethylenediamine, and the like, by methods which are well known in the art. The preparation of various suitable benzenesulfonyl chlorides and fluorides is described by Popoff et al in U.S. Pat. No. 3,453,099.

The fluorescent compounds useful in the chemiluminescent compositions of this invention may be defined broadly as water-soluble compounds, having an emission spectrum between 330 and 1,000 nanometers, which do not react with a hydrogen peroxide compound or the ester of oxalic acid on contact.

Numerous fluorescent compounds having the above-described properties are known. Many of these compounds are described in "Fluorescence and Phosphorescence" by Peter Pringsheim, Interscience Publishers, Inc., New York, New York 1949 and in "Dye Lasers" by F. P. Schafer, Editor, Springer Publishers, Berlin, (1973). Others are described in "The Colour Index", third edition, Volume 4, The Society of Dyers and Colourists and The American Association of Textile Chemists and Colorists (1971).

The wavelength emitted by the chemiluminescence of the compositions of this invention is essentially the same as the emission spectrum of the fluorescer compound employed.

Some specific examples of water soluble fluorescer compounds of the class defined are as follows:

Rhodamine B (C.I. 45170)
Rhodamine 6G Perchlorate
Sulforhodamine B (C.I. 45100)
Sulforhodamine 101
9,10-diphenylanthracene-2,6-disodiumsulfonate
3,9-perylenedisodiumsulfonate
3,10-perylenedisodiumsulfonate
Rhoadamine 6G (C.I. 45160)
Disodium fluorescein (C.I. 45350:1)
Sulforhodamine G (C.I. 45220) and the like.

The hydrogen peroxide compound employed in the compositions and processes of this invention may be an aqueous solution of hydrogen peroxide per se, or a hydrogen peroxide-producing compound, such as sodium perborate, potassium perborate, sodium carbonate peroxyhydrate, histidine perhydrate, and the like.

It has been found that the molar concentrations (moles per liter of solution) of the major components of the novel compositions described herein may vary considerably. It is only necessary that the components be present in sufficient concentration to obtain chemiluminescence. The molar concentration of the ester of oxalic acid normally is in the range of $10^{-3}$ to 5, preferably about $10^{-2}$ to 1.0. The molar concentration of the fluorescer compound used is from about $10^{-5}$ to $10^{-1}$, preferably $10^{-4}$ to $10^{-2}$. The molar concentration of the hydrogen peroxide compound used is from about $10^{-3}$ to 10.0, preferably $10^{-1}$ to 4.0. The optimum mole ratio of hydrogen peroxide compound to ester of oxalic acid used ranges from about 0.5 to 10.0.

The ingredients of the chemiluminescent compositions of this invention are kept separated until chemiluminescence is desired, when they may be admixed in a single step or in a series of steps. The order of admixing of the ingredients is usually not critical. The hydrogen peroxide compound and fluorescer compound may be dissolved in water and the oxalic acid ester is added thereto to initiate chemiluminescence. The oxalic acid ester may be added as a solid or in a suitable diluent. Alternatively, the oxalic acid ester and the fluorescer compound may be dissolved in water and the hydrogen peroxide compound added thereto to initiate chemiluminescence. Preferably, the oxalic ester, solid hydrogen peroxide compound and fluorescer are combined as a solid composition and when light is desired, added to water to initiate chemiluminescence.

The intensity of the chemiluminescence is relatively independent of the pH of the reaction medium. Variation of the pH from about 3 to 8 has no discernible effect on the intensity of light emitted in the visible range.

Superior intensity of chemiluminescence is obtained when the final mixture producing the luminescence is maintained at a temperature from about $-10°$ to $50°$ C, preferably from about $15°$ to about $40°$ C.

The invention is described in more detail in the following examples with specific reference to the most preferred mode of carrying out the invention.

EXAMPLE 1

Preparation of 3,5-Dichloro-2-Hydroxybenzenesulfonyl Chloride 3,5-Dichloro-2-hydroxybenzenesulfonyl chloride is prepared according to the procedure of Example 6 of U.S. Pat. No. 3,453,099, whereby 2,4-dichlorophenol (0.05 mole) is reacted with 2.5 moles of chlorosulfonic acid at room temperature. The mixture is poured onto ice and the acid layer decanted from the warmed mixture. The product is washed with ice water and recrystallized from carbon tetrachloride; m.p. $81°-83°$ C.

EXAMPLE 2

Preparation of 3,5-Dichloro-2-Hydroxy-N-(2-Dimethylaminoethyl)-N-Methylbenzenesulfonamide A clarified solution of 3,5-dichloro-2-hydroxybenzenesulfonyl chloride (47.64 grams; 0.18 mole) in 200 mls. of diethyl ether was added to a stirred solution of N,N,N'-trimethylethylenediamine (39.8 grams; 0.39 mole) in 200 mls. of diethyl ether over a period of 105 minutes and the reaction mixture was stirred at room temperature overnight.

The resulting precipitate was separated by filtration, washed with diethyl ether, reslurried in water, separated by filtration, washed with a small amount of water and dried to obtain 53.8 grams (91.5% yield) of crude product which melted at $197°$ to $200°$ C. Recrystallization of the crude material from 440 mls. of 50% aqueous ethanol gave 46.1 grams (78.3% yield) of pure material, m.p. $198°-200°$ C.

Calculated for $C_{11}H_{16}O_3N_2SCl_2$ (percent): C, 40.37; H, 4.93; N, 8.56; S, 9.80; Cl, 21.67. Found: C, 40.09; H, 4.78; N, 8.51; S, 9.80; Cl, 20.57, 20.71.

EXAMPLE 3

Preparation of Bis 2,4-Dichloro-6-[(2-Dimethylaminoethyl)methylsulfamoyl]phenyl Oxalate Dihydrochloride A mixture of the product of Example 2 (44.14 grams, 0.135 mole) and 400 mls. of water-washed, dry chloroform was heated to boiling and 100 mls. of distillate was collected to insure the removal of any water therein. The mixture was cooled to $35°$ to $40°$ C, a solution of oxalyl chloride (8.55 grams; 0.067 mole) in 60 mls. of water-washed, dry chloroform was added thereto dropwise and the reaction mixture was stirred overnight at room temperature.

The solid which precipitated overnight was separated by filtration, washed with chloroform and dried to obtain 47.45 grams (89.5% yield of crude product. The infrared spectrum of the crude material showed a single sharp band at 1775 $cm^{-1}$ which is indicative of oxalate ester carbonyl groups.

Following the procedure of Example 3 substituting 3-fluoro-4-hydroxy-N-(2-dimethylaminoethyl)-N-methylbenzenesulfonamide instead of the Example 2 products, one obtains bis 2-fluoro-4-[(2-dimethylaminoethyl)methylsulfamoyl]phenyl oxalate dihydrochloride is obtained.

Following the procedure of Example 3 substituting 3,5-dibromo-4-hydroxy-N-(2-di-n-hexylaminoethyl)-N-methylbenzenesulfonamide, one obtains bis 2,6-dibromo-4-[(2-di-n-hexylaminoethyl)methylsulfamoyl]phenyl oxalate dihydrochloride.

Following the procedure of Example 3 substituting 3,5-dibromo-4-hydroxy-N-(4-dimethylaminobutyl)-N-methylbenzenesulfonamide, one obtains bis 2,6-dibromo-4-[(4-dimethylaminobutyl)methylsulfamoyl]phenyl oxalate dihydrochloride.

Following the procedure of Example 3 substituting 3,5-dibromo-2-hydroxy-N-(2-dimethylaminoethyl)-N-n-hexylbenzenesulfonamide, one obtains bis 2,4-dibromo-6-[(2-dimethylaminoethyl)n-hexylsulfamoyl]phenyl oxalate dihydrochloride.

Following the procedure of Example 3 substituting 3,5-dichloro-2-hydroxy-N(2-piperidinoethyl)-N-methylbenzenesulfonamide, one obtains bis 2,4-dichloro-6-[(2-piperidinoethyl)methylsulfamoyl]phenyl oxalate dihydrochloride.

EXAMPLE 4

Addition of 2 mls. of 30% aqueous hydrogen peroxide to a solution containing 0.1 gram (0.000128 mole) of the product of Example 3 in 8 mls. of water containing a fluorescer concentration of $6.25 \times 10^{-2}$ gave the light emissions and durations listed in Table I. In each case the durations shown are approximate. The final composition was $1.28 \times 10^{-2}$ molar in oxalic acid ester, 1.86 molar in hydrogen peroxide and $5 \times 10^{-2}$ molar in fluorescer compound.

Table I

| Fluorescer | Light Emission | |
|---|---|---|
| | Color | Duration |
| Rhodamine B | Bright Orange-Red | 30 min. |
| Rhodamine 6G perchlorate | Orange | 10 min. |
| Sulforhodamine B | Bright Red-Orange | 10 min. |
| Sulforhodamine 101 | Bright Orange-Red | 10 min. |
| 9,10-diphenylanthracene-2,6-disodiumsulfonate (See Etiene et al, Bull. Soc. Chim. France - 835 (1949) | Bright Blue | 10 min. |

Table I-continued

| Fluorescer | Light Emission | |
|---|---|---|
| | Color | Duration |
| Mixture of 3,9- and 3,10-perlenedisodiumsulfonate (See C. Marschalk, Bull. Soc. Chim. France - 41, 74 (1928)) | Bright Blue | 10 min. |
| Rhodamine 6G | Orange | 10 min. |
| Disodium Fluorescein | Yellow-Green | 10 min. |
| Sulforhodamine G | Yellow-Pink | 10 min. |

EXAMPLE 5

Preparation of Bis 2,4-Dichloro-6-[(2-Trimethylammoniumethyl)methylsulfamoyl]phenyl Oxalate, Ditrifluoromethanesulfonate To a slurry of the oxalate ester of Example 3 (10.0 grams; 0.0128 mole) in 150 mls. of dry tetrahydrofuran was added methyl trifluoromethylsulfonate (4.9 grams; 0.0297 mole) followed immediately by the addition of potassium tert-butoxide (3.87 grams; 0.0336 mole). The reaction mixture was stirred overnight at room temperature and the resulting precipitate was separated by filtration. Recrystallization of the crude material from acetonitrile gave 6.71 grams (50.6% yield) of material which melted at 210°-215° C. Further recrystallization from acetonitrile raised the melting point to 227°-228° C.

Calculated (percent): $C_{28}H_{36}O_{14}Cl_4S_4F_6$: C, 32.22; H, 3.45; N, 5.37; Cl, 14.26; S, 12.34. Found: C. 30.86; H, 3.55; N, 5.41, Cl, 13.48; S, 13.20.

EXAMPLE 6

Following the procedure of Example 4 utilizing Rhodamine B as fluorescer and the product of Example 5 as the oxalic acid ester, an immediate bright orange-red emission was observed which lasted about 20 minutes.

EXAMPLE 7

Preparation of 3,5-Dichloro-4-Hydroxybenzenesulfonyl Chloride

Chlorosulfonic acid (460 grams; 3.95 moles) was added dropwise to a solution of 2,6-dichlorophenol (100 grams; 0.61 mole) in 200 mls. of carbon disulfide at 0°-5° C over a period of 105 minutes. The reaction mixture was stirred at 0°-5° C for a period of 1 hour after completion of the addition and the mixture was allowed to warm to room temperature. The mixture was then added very carefully (violent exotherm) to 2500 mls. of a mixture of ice and water. The resulting precipitate was separated by filtration, washed with water and dried under partial vacuum to obtain 150 grams of crude product. Recrystallization of the crude material from a mixture of 300 mls. of toluene and 300 mls. of heptane, after decolorization with activated charcoal, gave 1.27 grams (79.6% yield) of pure product, m.p. 123°-124° C.

EXAMPLE 8

Preparation of 3,5-Dichloro-4-Hydroxy-N-(2-Dimethylaminoethyl)-N-Methylbenzenesulfonamide A solution of the product of Example 7 (13.0 grams; 0.05 mole) in 60 mls. of diethyl ether was added dropwise over 1 hour to a solution of N,N,N'-trimethylethylenediamine (5.1 grams; 0.05 mole) in a mixture of 30 mls. of acetonitrile. The cream-colored solid which precipitated was separated by filtration, washed with dilute aqueous sodium bicarbonate and dried to obtain 10.5 grams (64% yield) of crude product. Recrystallization of the crude material from dimethylformamide gave 7.8 grams (47.7% yield) of pure product, m.p. 242°-243° C.

Calculated for: $C_{11}H_{16}N_2SCl_2O_3$ (percent): C, 40.37; H, 4.93; N, 8.56; Cl, 21.67; S, 9.80. Found: C, 40.08; H, 4.78; N, 8.48; Cl, 21.21; S, 9.55.

EXAMPLE 9

Preparation of Bis{2,6-Dichloro-4-[(2-Dimethylaminoethyl)methylsulfamoyl]phenyl}Oxalate, Dihydrochloride A suspension of the product of Example 8 (6.54 grams; 0.02 mole) in 60 mls. of dry pyridine was treated with 22 mls. of a toluene solution containing oxalyl chloride (1.2 grams; 0.01 mole). The gelatinous precipitate which formed was filtered to obtain 6.09 grams (78% yield) of crude product. The infrared absorption spectrum of the crude material indicated the presence of an oxalate carbonyl band and an amine hydrochloride band.

EXAMPLE 10

Following the procedure of Example 4 utilizing Rhodamine B as the fluorescer and the product of Example 9 as the oxalic acid ester an immediate bright orange-red emission is observed.

EXAMPLE 11

Following the procedure of Example 4 utilizing Rhodamine B as the fluorescer and bis 2-fluoro-4-[(2-dimethylamino ethyl)ethylsulfamoyl]phenyl oxalate dihydrochloride as the oxalic acid ester an immediate bright orange-red emission is observed.

EXAMPLE 12

Following the procedure of Example 4 utilizing Rhodamine B as the fluorescer and bis{2,6-dibromo-4-[(4-dimethylaminobutyl)methyl sulfamoyl]phenyl}oxalate dihydrochloride as the oxalic acid ester, an immediate bright orange-red emission is observed.

We claim:

1. A water-soluble ester of oxalic acid having the formula:

$$(Z)_n\text{-}\underset{Y^{\oplus}}{\underset{|}{\text{Ar}}}\text{-O-}\underset{\text{O}}{\overset{\text{O}}{\text{C}}}\text{-}\underset{\text{O}}{\overset{\text{O}}{\text{C}}}\text{-O-}\underset{Y^{\oplus}}{\underset{|}{\text{Ar}}}\text{-}(Z)_n \quad 2X^{\ominus}$$

wherein Z is selected from chloro, fluoro and bromo, n is 1 or 2, $X^-$ is an anion and $Y^+$ is a radical having the formula:

$$-\underset{\overset{\|}{\text{O}}}{\overset{\overset{\text{O}}{\|}}{\text{S}}}-\underset{\overset{|}{R_1}}{\text{N}}-(CH_2-)_m\underset{\overset{|}{R_4}}{\overset{\overset{R_2}{|}}{\text{N}^{\oplus}}}-R_3$$

wherein $R_1$ is an alkyl having 1 to 6 carbon atoms, $R_2$ and $R_3$ independently represent alkyl having 1 to 6 carbon atoms or together with the nitrogen atom form a piperidine ring, $R_4$ is selected from hydrogen and alkyl having 1 to 6 carbon atoms, and m is an integer from 1 to 4.

2. A water-soluble esters according to claim 1 wherein $X^-$ is an anion selected from chloride, bromide, fluoride, trifluoromethanesulfonate, methanesulfonate, p-toluenesulfonate and methosulfate.

3. Bis{2,6-dichloro-4-[(2-dimethylaminoethyl)methylsulfamoyl]phenyl}oxalate dihydrochloride.

4. Bis{2,4-dichloro-6-[(2-dimethylaminoethy)methylsulfamoyl]phenyl}oxalate dihydrochloride.

5. Bis{2,4-dichloro-6-[(2-dimethylaminoethyl)methylsulfamoyl]phenyl}oxalate ditrifluoromethanesulfonate.

6. Bis{2-chloro-4-[(2-dimethylaminoethyl)methylsulfamoyl]phenyl}oxalate dihydrochloride.

7. Bis{2,6-dibromo-4-[(2-dimethylaminoethyl)methylsulfamoyl]phenyl}oxalate dihydrochloride.

8. Bis{2,4-dibromo-6-[(2-dimethylaminoethyl)methylsulfamoyl]phenyl}oxalate dihydrochloride.

9. Bis{2,4-dibromo-6-[(2-dimethylaminoethyl)methylsulfamoyl]phenyl}oxalate ditrifluoromethanesulfonate.

10. Bis{2-bromo-4-[(2-dimethylaminoethyl)methylsulfamoyl]phenyl}oxalate dihydrochloride.

11. Bis{3-fluoro-4-[(2-dimethylaminoethyl)methylsulfamoyl]phenyl}oxalate dihydrochloride.

12. Bis{2-fluoro-4-[(2-dimethylaminoethyl)methlysulfamoyl]phenyl}oxalate dihydrochloride.

13. A composition useful for generating chemiluminescent emission comprising an aqueous solution of (a) a water-soluble ester of oxalic acid defined by claim 1 and (b) a water-soluble organic fluorescer having a spectral emission in the range from about 330 to 1,000 nanometers, in proportions capable of producing chemiluminescence on reaction with hydrogen peroxide.

14. A composition defined by claim 13 wherein the anion of said ester of oxalic acid is selected from chloride, bromide, fluoride, trifluoromethanesulfonate, p-toluenesulfonate and methosulfate.

15. A composition defined by claim 14 wherein said oxalate ester is bis{2,6-dichloro-4-[(2-dimethylaminoethyl)methylsulfamoyl]phenyl}oxalate dihydrochloride.

16. A composition defined by claim 14 wherein said oxalate ester is bis{2,4-dichloro-6-[(2-dimethylaminoethyl)methylsulfamoyl]phenyl}oxalate dihydrochloride.

17. A composition defined by claim 14 wherein said oxalate ester is bis{2,4-dichloro-6-[(2-dimethylaminoethyl)methylsulfamoyl]phenyl}oxalate ditrifluoromethanesulfonate.

18. A composition defined by claim 14 wherein said oxalate ester is bis{2-chloro-4-[(2-dimethylaminoethyl)methylsulfamoyl]phenyl}oxalate dihydrochloride.

19. A composition defined by claim 14 wherein said oxalate ester is bis{2,6-dibromo-4-[(2-dimethylaminoethyl)methylsulfamoyl]phenyl}oxalate dihydrochloride.

20. A composition defined by claim 14 wherein said oxalate ester is bis{2,4-bromo-6-[(2-dimethylaminoethyl)methylsulfamoyl]phenyl}oxalate dihydrochloride.

21. A composition defined by claim 14 wherein said oxalate ester is bis{2,4-dibromo-6-[(2-dimethylaminoethyl)methylsulfamoyl]phenyl}oxalate ditrifluoromethanesulfonate.

22. A composition defined by claim 14 wherein said oxalate ester is bis{2-bromo-4-[(2-dimethylaminoethyl)methlysulfamoyl]phenyl}oxalate dihydrochloride.

23. A composition defined by claim 14 wherein said oxalate ester is bis{3-fluoro-4-[(2-dimethylaminoethyl)methylsulfamoyl]phenyl}oxalate dihydrochloride.

24. A composition defined by claim 14 wherein said oxalate ester is bis{2-fluoro-4-[(2-dimethylaminoethyl)methylsulfamoyl]phenyl}oxalate dihydrochloride.

25. A composition useful for generating chemiluminescent emission comprising an aqueous solution of (a) hydrogen peroxide or a source of hydrogen peroxide selected from the group consisting of sodium perborate, potassium perborate, sodium carbonate peroxyhydrate, and histidine perhydrate, (b) a water-soluble fluorescer compound having a spectral emission from about 330 to 1,000 nanometers, and (c) a water-soluble ester of oxalic acid of claim 1, in proportions capable of producing a chemiluminescent reaction when the defined composition is in water.

26. A process for generating chemiluminescence comprising adding an effective amount of hydrogen peroxide or a source of hydrogen peroxide selected from the group consisting of sodium perborate, potassium perborate, sodium carbonate peroxyhydrate, and histidine perhydrate into an aqueous solution of a water-soluble ester of oxalic acid defined by claim 1 and a water-soluble organic fluorescer compound having a spectral emission in the range from 330 to 1,000 nanometers.

27. A process for generating chemiluminescence comprising adding an effective amount of a water-soluble oxalate ester defined by claim 1 into an aqueous solution of hydrogen peroxide or a source of hydrogen peroxide selected from the group consisting of sodium perborate, potassium perborate, sodium carbonate peroxyhydrate, and histidine perhydrate and a water-soluble organic fluorescer compound having a spectral emission from about 330 to 1,000 nanometers.

28. A composition useful for generating chemiluminescent emission comprising a dry mixture of an oxalic ester defined by claim 1, a solid hydrogen peroxide compound selected from the group consisting of sodium perborate, potassium perborate, sodium carbonate peroxyhydrate, and histidine perhydrate and a solid fluorescer in proportions capable of producing a chemiluminescent reaction in water.

29. A composition according to claim 28 wherein the solid hydrogen peroxide compound is sodium perborate.

30. A process for generating chemiluminescence comprising mixing the composition of claim 28 with water.

* * * * *